United States Patent
Chun et al.

(10) Patent No.: US 6,939,719 B2
(45) Date of Patent: *Sep. 6, 2005

(54) EQUIPMENT OF LOCAL STREAMING POTENTIAL MEASUREMENT FOR MONITORING THE FOULING PROCESS IN HOLLOW-FIBER FILTRATIONS OF NANO-COLLOIDAL SUSPENSION

(75) Inventors: Myung-Suk Chun, Seoul (KR); Jae-Jin Kim, Seoul (KR); Sang Yup Lee, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 10/821,856

(22) Filed: Apr. 12, 2004

(65) Prior Publication Data

US 2004/0266017 A1 Dec. 30, 2004

Related U.S. Application Data

(62) Division of application No. 09/906,696, filed on Jul. 18, 2001, now Pat. No. 6,727,099.

(51) Int. Cl.[7] ............................................. G01N 27/416
(52) U.S. Cl. .................... 436/151; 73/38; 73/64.56; 73/61.73; 210/741; 210/746
(58) Field of Search .................... 422/69, 81; 436/151; 73/38, 64.56

(56) References Cited

U.S. PATENT DOCUMENTS

| 6,463,790 B1 | 10/2002 | Chun et al. |
| 6,727,099 B2 * | 4/2004 | Chun et al. ................. 436/151 |

FOREIGN PATENT DOCUMENTS

| JP | 1038836 | 2/1989 |
| JP | 6247545 | 9/1994 |
| JP | 8101158 | 4/1996 |
| JP | 11197472 | 7/1999 |

* cited by examiner

*Primary Examiner*—Jill Warden
*Assistant Examiner*—Sam P. Siefke
(74) *Attorney, Agent, or Firm*—Finnegan, Henderson, Farabow, Garrett & Dunner, LLP

(57) ABSTRACT

The present invention relates to an apparatus for monitoring the progress of membrane fouling that occurs on pores as well as on the surface of a membrane by means of variations of zeta potential ($\zeta$) of a hollow-fiber membrane according to time passage of filtration of a suspension, wherein colloid particles, biopolymers and other inorganic particles are dispersed, and the method thereof. Moreover, the present invention also relates to a method to identify the effect of concentration polarization layer and cake layer which can vary according to the axial position of a hollow-fiber and the developing progress of a membrane fouling by measuring the position-dependent zeta potential of the hollow-fiber membrane.

5 Claims, 4 Drawing Sheets

EQUIPMENT OF LOCAL STREAMING POTENTIAL MEASUREMENT FOR MONITORING THE FOULING PROCESS IN HOLLOW-FIBER FILTRATIONS OF NANO-COLLOIDAL SUSPENSION

This is a division of application Ser. No. 09/906,696, filed Jul. 18, 2001 now U.S. Pat. No. 6,727,099, which claims the benefit of priority under 35U.S.C. §119 of Korean Application No. 2001-25970, filed May, 12, 2001, all of which are incorporated herein by reference.

BACKGROUND OF THE INVENTION

1. Field of the Invention

The present invention relates to an apparatus for monitoring the progress of membrane fouling that occurs on pores as well as on the surface of a membrane by means of variations of zeta potential ($\zeta$) of a hollow-fiber membrane measured according to time passage of filtration of a suspension, wherein colloid particles, biopolymers and other inorganic particles are dispersed, and the method thereof. Moreover, the present invention also relates to a method to identify the effect of concentration polarization layer and cake layer which can vary according to the axial position of a hollow-fiber and the subsequent developing progress of a membrane fouling by measuring the position-dependent zeta potential of the hollow-fiber membrane.

2. Description of the Related Art

In conventional methods, measurements of streaming potential of a membrane have been implemented by employing either a flat-plate type or a tubular membrane and the related studies have been largely restricted to charged property of membrane surface or electrokinetic phenomena. Therefore, there is a need for the development of a technology that can interpret the fouling progress of a given membrane via changes in zeta potential according to time passage of filtration as well as measurement of streaming potential of a hollow-fiber membrane.

Zeta potential, being defined based on electrostatic and electrokinetic principles, is known to provide useful real-time information on the surface property and the interaction between membrane and particles in actual operational situations and physicochemical conditions without incurring structural change of membrane or disturbance of flow condition. That is, zeta potential can not only provide information on electrostatic field when the membrane surface is in contact with a flowing solution but can be also an important physical quantity related to a criterion of membrane fouling resulted from adsorption or deposition of particles thus determining the property and performance of a membrane.

In the present invention, electrodes were installed both inside and outside of an inlet and an outlet of a hollow-fiber membrane, respectively, to measure the streaming potential. The difference between streaming potentials perceived simultaneously at these electrodes were used to evaluate the value of zeta potential.

The conventional apparatus and methods related to the present invention are described hereunder.

Ricq et al. [Journal of Membrane Science, 114(1996), 27–38] studied the properties of the initial virgin and the fouled membranes after filtration of a tubular inorganic membrane by measuring zeta potential and analyzing permeate flux. They installed platinum electrodes such that they penetrated the internal channel of a membrane and measured the streaming potential difference and permeate flux, however, the membrane used was not a hollow-fiber membrane but a tubular membrane and also the measurements were not made at various positions but at the inlet.

Japanese Pat. No. 62-47545 discloses a method to measure streaming potential as a way to identify the property of zeta potential inside of a hollow-shaped cylindrical tube. This method relates to the measurement of streaming potential of the internal wall of a cylindrical tube, a kind of a pipe, unlike the apparatus of the present invention which relates to a hollow-fiber having membrane pores. This method enables to measure the zeta potential of the internal wall since a given solution can flow through the cylindrical tube, however, it cannot measure the property of membrane pores located on the radial wall of a hollow-fiber as shown in the present invention.

Japanese Published Pat. Appln. No. 11-197472 discloses a method to analyze fouling in a given separation membrane as a way to identify the fouling of a reverse osmosis membrane. This method enables to identify the fouling of a flat-plate reverse osmosis membrane by comparing the zeta potentials on membrane surface before and after the fouling and also sets up the washing conditions of the membrane. However, this method is only related to the application of the result of zeta potential to the observation of membrane fouling and is not related to the method or the apparatus of measuring streaming potential. The example 2 of the present invention also shows that the zeta potential changes according to the membrane fouling.

Szymczyk et al. conducted a study on zeta potential according to the change in ionic concentration of electrolytes by installing an Ag/AgCl electrode at each given point on both an upper and a lower region of plane inorganic membrane [Journal of Membrane Science, 134(1997), 59–66].

Japanese Published Pat. Appln. No. 8-101158 discloses a method to measure streaming potential of porous materials and Japanese Published Pat. Appln. No. 10-38836 discloses an apparatus to measure streaming potential.

These methods and apparatus, being designed for porous materials, cannot be applied to a hollow-fiber membrane and also cannot be used in measuring zeta potentials at local positions.

SUMMARY OF THE INVENTION

It is essential to provide fine installments of electrodes which carry out measurements of minute streaming potential difference in order to obtain the membrane zeta potential. A hollow-fiber membrane is not advantageous in that it has a very narrow internal diameter unlike a flat-plate or a tubular membrane, and this results in difficulty when installing internal electrodes and also becomes liable to damage the hollow-fiber or disturb the liquid flow. Moreover, the cross-flow filtration enables to generate a concentration polarization layer as the filtration is run along the axial direction and the continued permeation results in change in particle concentrations as well as the pressure drop, according to the axial position.

The present invention installed electrodes both inside and outside of an inlet and an outlet of a hollow-fiber membrane, respectively, and also provided a device to sense the minute change of streaming potential difference generated by the minute pressure difference across the membrane pores.

The present invention succeeded in monitoring the progress of membrane fouling over time by evaluating the zeta potential of a hollow-fiber membrane by continuously measuring the streaming potential in two given positions according to time passage of filtration of a given suspension.

Figure 1:
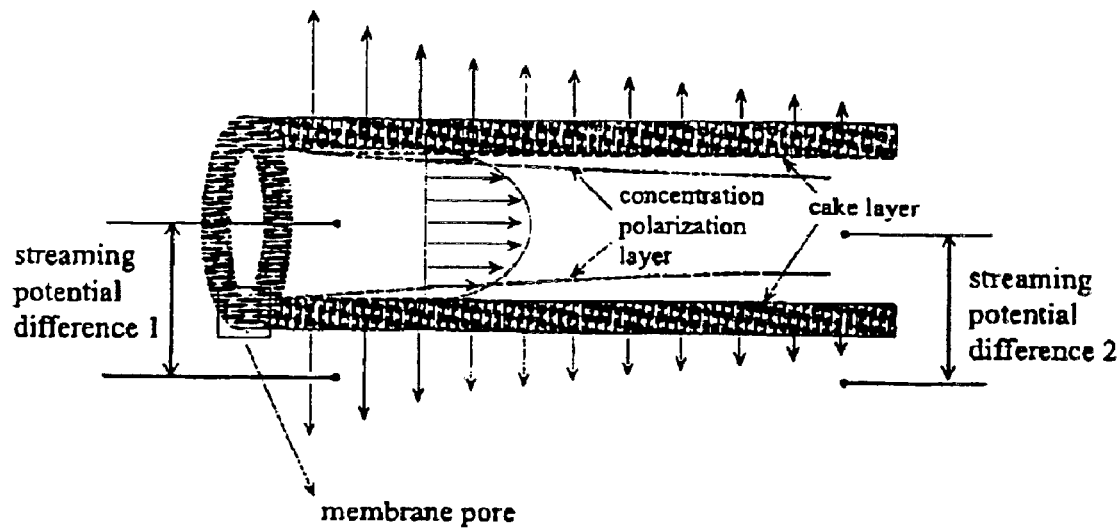
FIG. 1 is a diagram that shows a concentration polarization layer as well as a cake(or gel) layer generated inside a hollow-fiber membrane by cross-flow filtration and the resulting difference in local streaming potential.

[Code Explanation]
1. thermostated feed tank
2. solvent delivery pump
3. conductance meter
4. pH meter
5. connecting part of membrane module
6. main body of membrane module
7. clamping part of membrane module
8. internal electrode of a hollow-fiber membrane
9. external electrode of a hollow-fiber membrane
10. hollow-fiber membrane
11. minute flow-control valve
12. multi-channel digital multi-meter
13. computer
14. pressure gauge
15. pressure gauge connecting aperture
16. sealing ring
17. epoxy resin potting

DETAILED DESCRIPTION OF THE INVENTION

The present invention relates to an apparatus and the method of measuring local streaming potential for monitoring the progress of membrane fouling over time in the course of filtration with hollow-fiber membrane.

To achieve the above-mentioned goal, the inventors of the present invention prepared an apparatus which comprises a feed tank to reserve feed solution in a state of colloidal suspension; a membrane module with several hollow-fibers as well as a connecting part and electrodes to measure streaming potential; a means to deliver feed solution from the feed tank to the inside of the hollow-fiber membranes; a means to measure physical properties of said feed solution; a means to measure the transmembrane pressure differences between the inside and the outside of a hollow-fiber at both an inlet and an outlet of a membrane module and a means to control the transmembrane pressure differences; a means to simultaneously measure and record the differences in local streaming potential being obtained from the above electrodes; and a means to obtain the value of zeta potential ($\zeta$) of a hollow-fiber membrane by using the physical properties, transmembrane pressure difference and the difference in streaming potential.

This invention will be better understood with the following figures.

FIG. 1 shows a diagram that depicts a concentration polarization layer as well as a cake layer generated inside a hollow-fiber membrane due to cross-flow filtration and the resulting local streaming potential difference.

Figure 2:
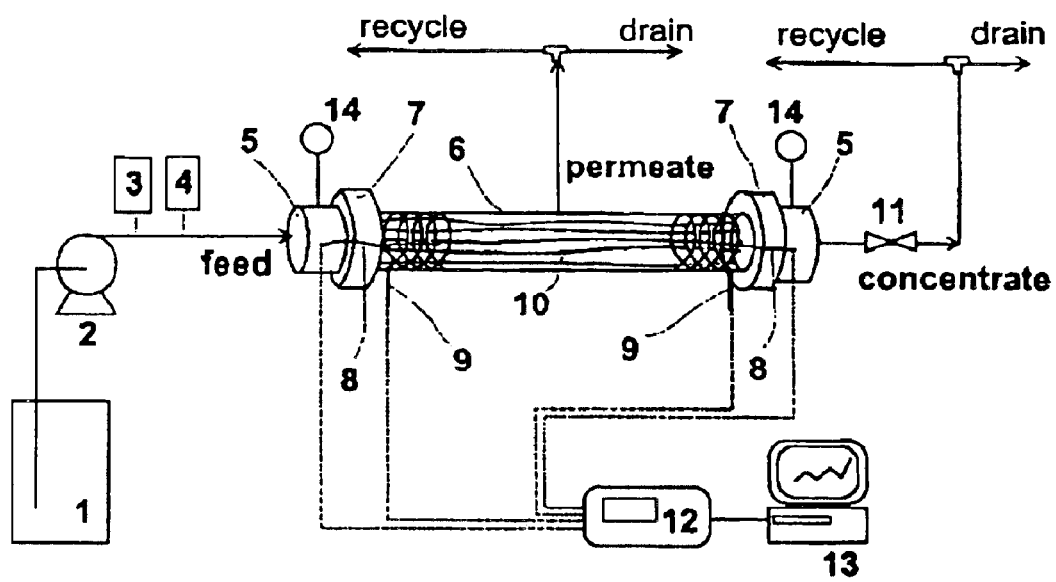
FIG. 2 is a schematic diagram of the apparatus of the present invention that enables to measure the difference in local streaming potential of a hollow-fiber membrane by cross-flow filtration.

FIG. 2 is a schematic diagram of the apparatus of the present invention that can measure local streaming potential difference of a hollow-fiber membrane due to cross-flow filtration. As shown in FIG. 2, the apparatus of measuring streaming potential according to the present invention comprises a thermostated feed tank 1 to reserve feed solution in a state of colloidal suspension; two means 3 and 4 to measure physical properties of said feed solution; the body of membrane module 6 equipped with electrodes 8 and 9 to measure streaming potential difference as well as a hollow-fiber membrane 10; a fine flow-control valve 11 to adjust transmembrane pressure difference present between the inside and outside of the hollow-fiber 10; a pressure gauge 14 that measures the transmembrane pressure difference both at an inlet and an outlet of a membrane module; connecting parts 5 and 7 which are parts of membrane module that link between membrane module and flow channel; two means 12 and 13 to display and record data being obtained from the above-mentioned measuring means; and a means to calculate the value of zeta potential ($\zeta$) of the hollow-fiber membrane 10.

Figure 3:
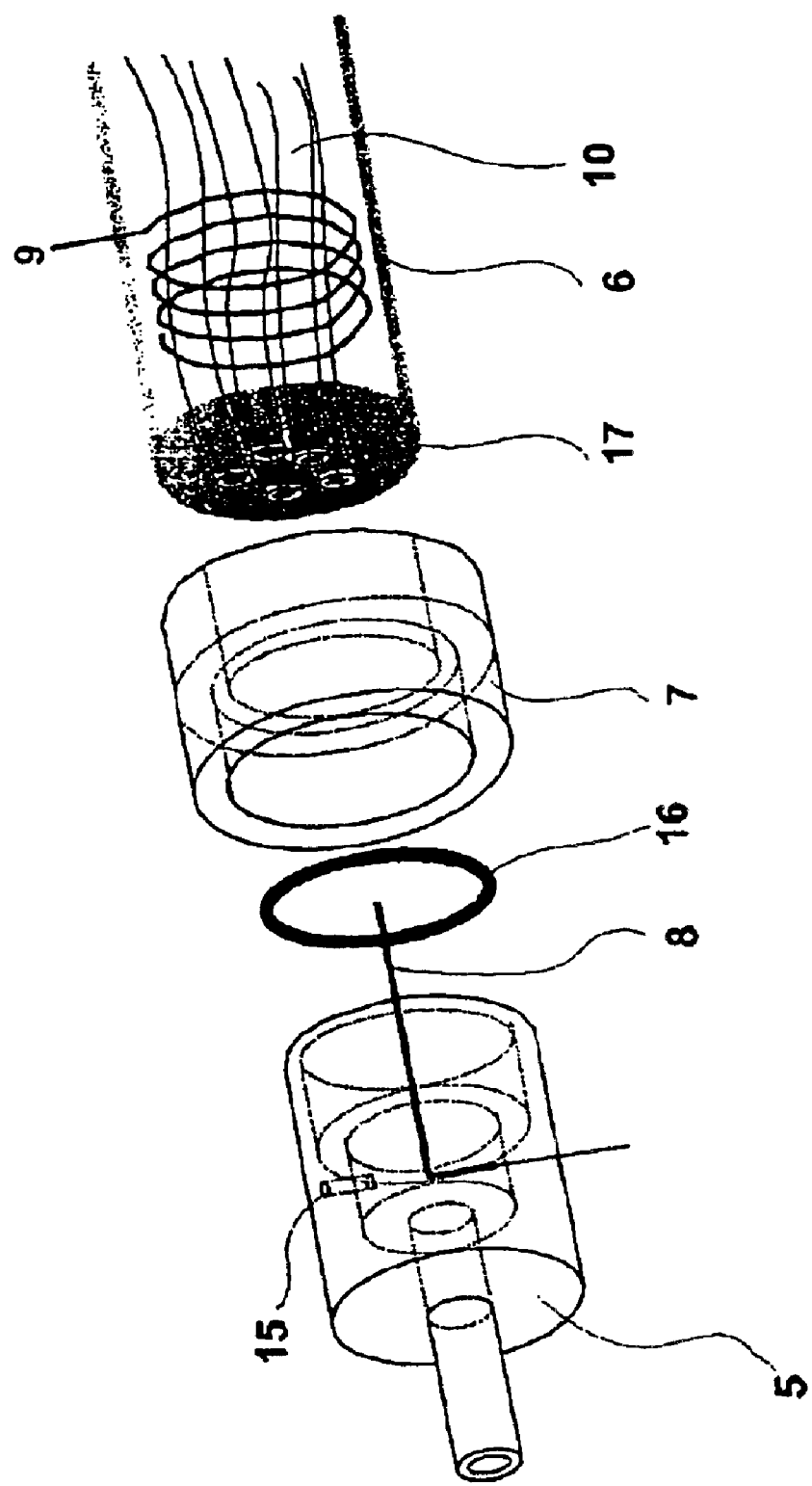
FIG. 3 shows an exploded view of a hollow-fiber membrane module used in the apparatus of the present invention measuring streaming potential difference.

FIG. 3 is an exploded view of the connecting part between membrane module and the flow channel, which shows a connecting part 15, electrodes 8 and 9 to measure streaming potential difference, a clamping part 14 of membrane module, a sealing ring 16 to prevent fluid leakage at the connecting part, the hollow-fiber membrane 10 wherein the actual filtration takes place, a potting region 17 cured by epoxy resin to separate the permeate from the feed solution, and the body 6 of cylindrical membrane module containing the above-mentioned parts.

The relative cooperation of the respective parts of the membrane module is set forth hereunder.

An Ag/AgCl (or platinum) wire-type electrode 8 with 0.25 mm in diameter, which takes about 6% of the internal cross-sectional area of a hollow-fiber, is installed inside the hollow-fiber membrane 10, where the actual filtration of feed solution takes place, to allow undisturbed liquid flow while a spiral electrode 9 made of the same material is installed on the corresponding external positions of the hollow-fiber so that it can sense the minute streaming potential difference according to the minute pressure difference.

The permeation of suspension due to pressure difference results in change in ionic fluid flow and charge distribution within a solution in the hollow-fiber membrane pores. Therefore, it generates a difference in streaming potential between the upper and the lower regions of membrane pores and the difference can be detected by a pair of electrodes consisting of an internal electrode 8 and the external electrode 9. The internal electrode 8 is inserted into the inside of the hollow-fiber membrane mounted on the cylindrical membrane module by means of the clamping part 7 of the membrane module, and the varying values detected in each electrode are measured by using multi-channel digital multi-meter 12.

The method of measuring streaming potential can be further delineated as follows. A given solution is supplied from the thermostated feed tank 1 of feed solution through the membrane module connecting part 5 to the hollow-fiber membrane 10 by means of a solvent delivery pump 2, and subsequently the respective conductance and pH are measured by using a conductance meter 3 and a pH meter 4.

The pressure is generally proportional to the flow rate, and thus the transmembrane pressure can be properly adjusted by using a minute flow-control valve 11. The minute flow control valve 11, installed at an outlet of a concentrate, may be able to precisely control the flow rate to the extent of 0.3% of the maximum flowrate.

The streaming potential ($\Delta V$) generated between the upper and the lower regions of membrane pores at a given position of the hollow-fiber membrane is measured by using a multi-channel digital multi-meter 12 via Ag/AgCl electrodes 8 and 9 installed inside and outside of the given position, respectively, and recorded in a computer 13.

The zeta potential can be obtained by plugging the values of streaming potential ($\Delta V$), generated from a given pressure difference ($\Delta P$), dielectric constant $\in$, conductivity of a solution $\lambda$, and viscosity of a solution $\eta$ into the following Helmholtz-Smoluchowski equation (1).

$$\frac{\Delta V}{\Delta P} = \frac{\varepsilon \zeta}{\lambda \eta} \quad (1)$$

This invention is explained in more detail based on the following examples, however, they should not be construed as limiting the scope of this invention.

Example 1

A given solution can have various pH values in the course of filtration of the hollow-fiber membrane. In measuring zeta potential according to pH change, it is usually quite essential to measure an isoelectric point. After installing several hollow-fiber ultrafiltration membranes (Model PM100, Internal diameter; 1.0 mm, KOCH Membrane System Inc., MA, USA) made of polysulfonate having asymmetric membrane pores, pH was modified in the presence of 1.0 mM aqueous solution of potassium chloride, a symmetric monovalent electrolyte. Then, streaming potential was measured at two different positions, at an inlet and at an outlet of a hollow-fiber membrane, under the pressure difference of less than 0.4 $kg_f/cm^2$ across the membrane pores.

The results of the application of the above equation (1) were reliable when the zeta potential difference of the membrane was less than 5% between two directions, wherein one of the flow directions of permeate was directed outside from the inside of the hollow-fiber membrane while the other is directed in the opposite way. As the pH increased, according to the results, the zeta potential of a hollow-fiber membrane changed from negative to positive and the isoelectric point was formed around pH 9.4.

The absolute value of zeta potential at an outlet of a hollow-fiber membrane was lower than that at an inlet and this is ascribed to the fact that the permeation of a given solution is continued while the flow of feed solution is directed to the axial direction of the hollow-fiber membrane and thus the flow rate becomes to decrease as it goes to the outlet and also the amount of the charged ions become depleted. The results are shown in the FIG. 4.

Example 2

As a way to monitor the change in zeta potential of a given solution according to time passage of filtration, wherein particles are suspended in feed solution, several hollow-fiber ultrafiltration membranes (Model PM100, Internal diameter; 1.0 mm, KOCH Membrane System Inc., MA, USA) made of polysulfonate having asymmetric membrane pores were installed on membrane modules. Then, an aqueous solution containing a biopolymer of 300 ppm of bovine serum albumin (BSA) was filtered and then streaming potential was measured at two different positions both at an inlet and at an outlet of a hollow-fiber membrane. The pressure difference across the membrane pores was less than 0.2 $kg_f/cm^2$, the concentration of potassium chloride as an electrolyte was 1.0 mM and the pH of the solution was 6.0. It is already known that, at pH 6.0, the pores of a hollow-fiber membrane are positively charged as in the example 1 while the surface of BSA is negatively charged.

Figure 5:
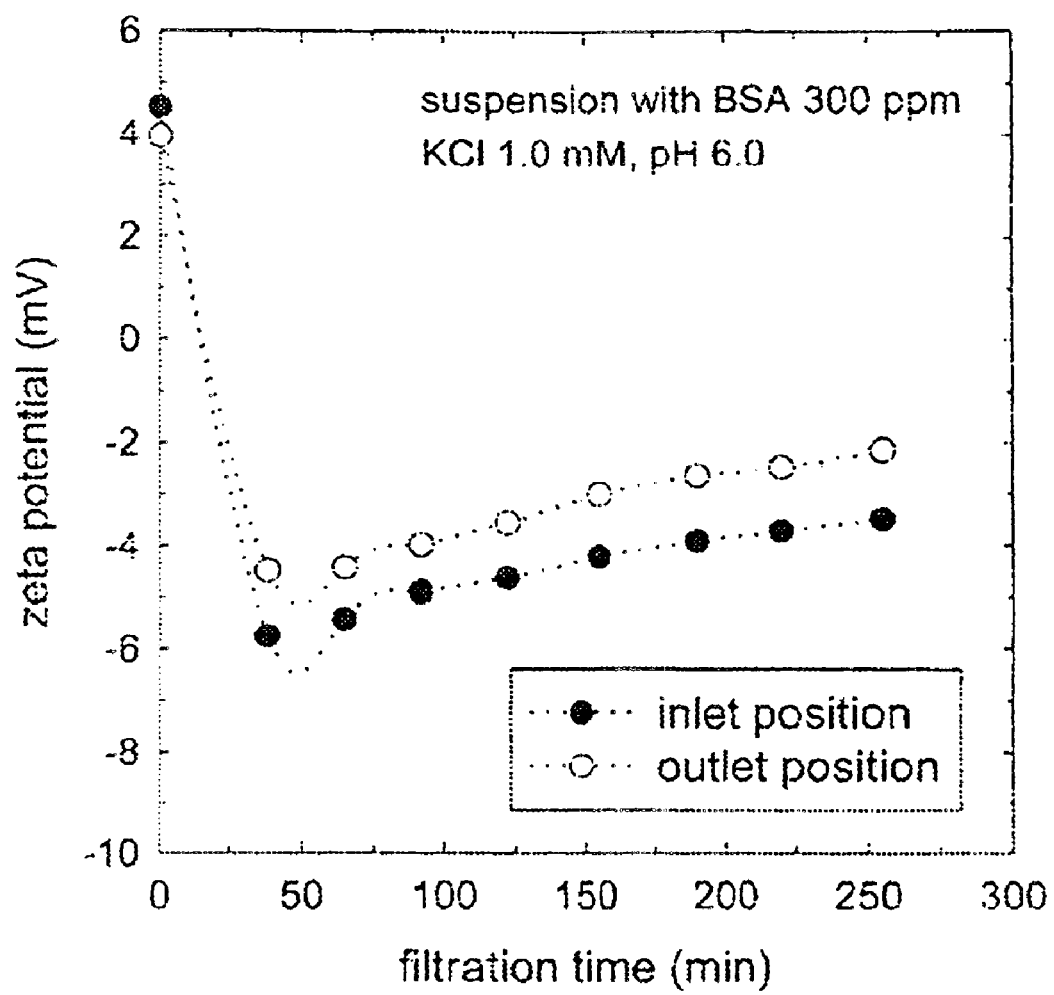
FIG. 5 is a graph that shows the change in zeta potential at an inlet and an outlet of a hollow-fiber membrane measured according to the time passage under a constant pH as well as a constant ion concentration of a symmetric monovalent electrolyte while performing filtration of a biopolymer protein solution.

The FIG. 5 shows the result of filtration progress, which reveals that the absolute value of the zeta potential was higher at the inlet than that at the outlet and this is consistent with the example 1. The zeta potential changed from positive to negative about 20 min after the start of the filtration and this indicates that the properties of the charged membrane must have been changed during the filtration process due to the adsorption or deposition of BSA particles, which were negatively charged at pH 6.0, onto the surface of the membrane. The absolute value of zeta potential decreases as the filtration proceeds and even a faster decreasing rate at the outlet; this appears to be due to the weakened electrokinetic flow resulted from the narrowed membrane pores due to the continued adsorption or deposition of BSA particles.

Comparative Example 1

Figure 4:
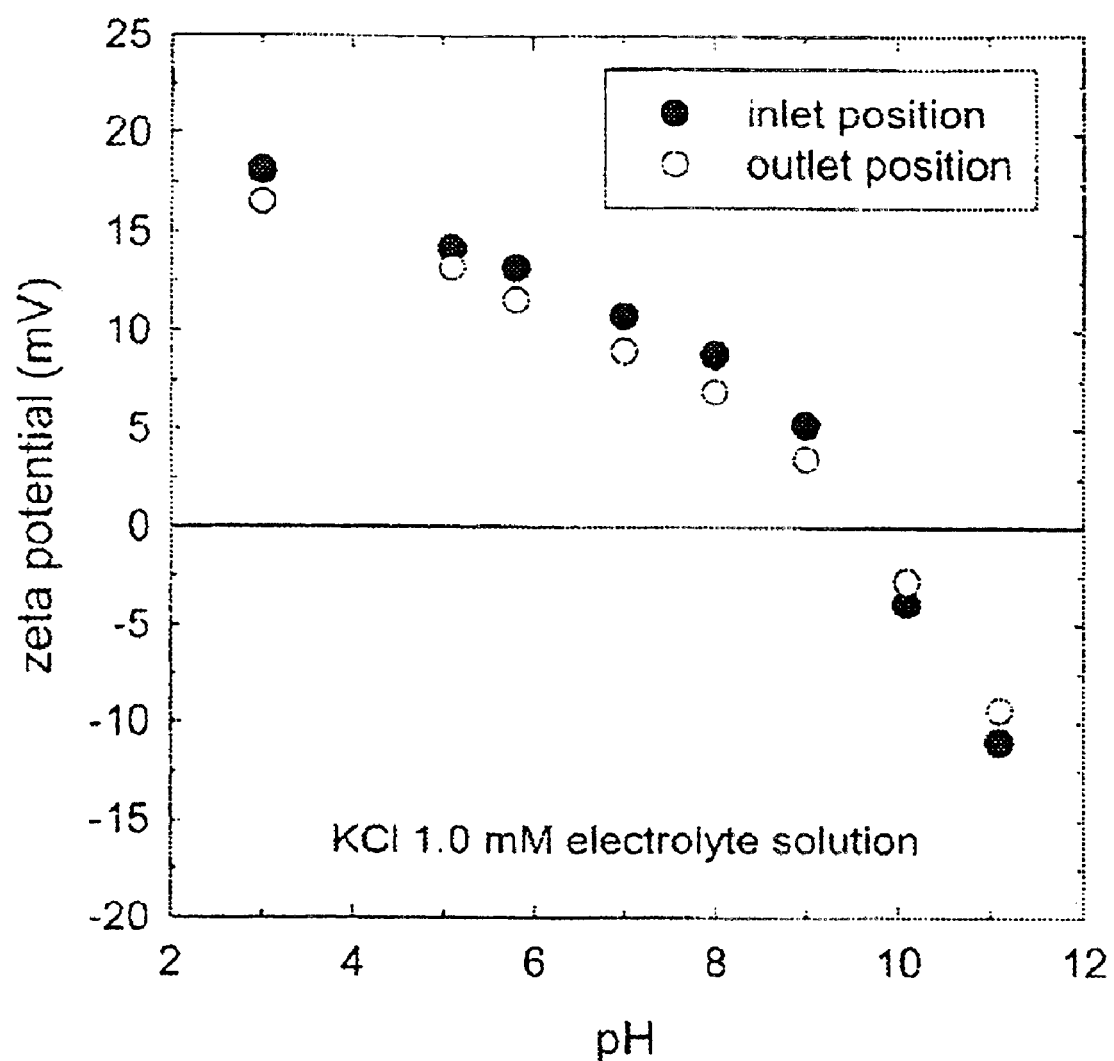
FIG. 4 is a graph that shows zeta potential at an inlet and an outlet of a hollow-fiber membrane measured according to the change of pH under a constant ion concentration of a symmetric monovalent electrolyte.

The zeta potentials according to filtration progress and the location of a membrane were measured by using the apparatus in the example 1 as shown in the examples 1, 2, and FIGS. 4 and 5, however, there are no reports on these results in the prior art.

As mentioned above, the present invention provides a novel apparatus and a novel method to obtain zeta potential influenced by a concentration polarization layer and a cake (or gel) layer which can vary according to the axial position in a given hollow-fiber membrane. The ability to obtain the zeta potential in the present invention in the course of filtration of a given suspension with a hollow-fiber according to time passage can also help to identify the characteristics of physicochemical interactions on membrane pores and on membrane surface as well as to monitor the progress of membrane fouling. These are essential in studying the downstream for the highly efficient filtration with a hollow-fiber membrane. Further, the present invention can also provide critical data that can be used in studying the electrokinetic properties, charged characteristics, hydrophilicity and the level of substituted functional as well as ionic groups according to modifications.

What is claimed is:

1. An apparatus for measuring local streaming potential of a membrane for monitoring the progress of membrane fouling in the course of filtration of a hollow-fiber membrane, wherein said apparatus comprises
    a feed tank to reserve feed solution in a state of colloidal suspension;
    a delivery pump to deliver said feed solution through a feed line;
    a membrane module with a plurality of hollow-fibers through which said feed solution is introduced from said feed line and released through an exit line;
    at least one electrode installed externally of a hollow-fiber located at the inlet of the membrane module;
    at least one electrode installed inside the hollow-fiber located at the inlet of the membrane module;

at least one electrode installed externally of a hollow-fiber located at the outlet of the membrane module;

at least one electrode installed inside the hollow-fiber located at the outlet of the membrane module;

a means to measure physical properties of said feed solution being introduced into a membrane module;

a pressure meter that measures the transmembrane pressure difference both at the inlet and outlet of a membrane module;

a flow-control valve in said exit line used to adjust the transmembrane pressure difference;

a means to display and record data obtained from the above-mentioned measuring devices; and a means to calculate the value of zeta potential (ζ) of a hollow-fiber membrane.

2. The apparatus according to claim 1, wherein said hollow-fiber membrane is bundled with an epoxy resin potting to separate feed solution and permeate.

3. The apparatus according to claim 1, wherein the electrodes installed inside said hollow-fiber membrane are wire-type Ag/AgCl electrodes of 0.25 mm in diameter that cover about 6% of the total internal cross-sectional area while the electrodes installed outside said hollow-fiber membrane are spiral electrodes of the same material.

4. The apparatus according to claim 1, wherein said flow-control valve is able to precisely control the flow rate to the extent of 0.3% of the maximum flow rate.

5. The apparatus according to claim 1, wherein the data obtained from the devices are displayed and recorded using a multi-channel digit multi-meter and a computer, and the value of zeta potential (ζ) of the hollow-fiber membrane calculated by using the equation (1), $$\frac{\Delta V}{\Delta P} = \frac{\varepsilon \zeta}{\lambda \eta} \quad (1)$$

wherein ΔV is streaming potential difference; ΔP is pressure difference; ∈ is the the dielectric constant; λ is the conductivity of a solution; and is the viscosity of a solution.

* * * * *

UNITED STATES PATENT AND TRADEMARK OFFICE
CERTIFICATE OF CORRECTION

PATENT NO. : 6,939,719 B2
DATED : September 6, 2005
INVENTOR(S) : Chun et al.

It is certified that error appears in the above-identified patent and that said Letters Patent is hereby corrected as shown below:

<u>Column 8,</u>
Line 18, "is the the dielectric" should read -- is the dielectric --.
Line 19, "and is" should read -- and η is --.

Signed and Sealed this

Eighth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,939,719 B2
DATED : September 6, 2005
INVENTOR(S) : Myung-Suk Chun It is certified that error appears in the above-identified patent and that said Letters Patent is hereby corrected as shown below:

Title page,
Item [75], Inventors, remove "Jae-Jin Kim, Seoul (KR)" and "Sang Yup Lee, Seoul (KR).".

Signed and Sealed this

Thirty-first Day of January, 2006

JON W. DUDAS
*Director of the United States Patent and Trademark Office*